(12) United States Patent
Munisekhar

(10) Patent No.: US 10,179,148 B2
(45) Date of Patent: Jan. 15, 2019

(54) KERATOLYTIC COMPOSITION WITH ANTI-ALLERGIC ANTI-INFLAMMATORY PROPERTIES

(71) Applicant: Medasani Munisekhar, Hyderabad (IN)

(72) Inventor: Medasani Munisekhar, Hyderabad (IN)

(*) Notice: Subject to any disclaimer, the term of this patent is extended or adjusted under 35 U.S.C. 154(b) by 721 days.

(21) Appl. No.: 14/571,054

(22) Filed: Dec. 15, 2014

(65) Prior Publication Data

US 2015/0164941 A1    Jun. 18, 2015

Related U.S. Application Data

(63) Continuation of application No. 10/551,001, filed as application No. PCT/IN2004/000069 on Mar. 26, 2004, now abandoned.

(30) Foreign Application Priority Data

Mar. 27, 2003    (IN) .............................. 185/KOL/2003

(51) Int. Cl.
| | | |
|---|---|---|
| *A61K 33/02* | (2006.01) | |
| *A61K 8/20* | (2006.01) | |
| *A61K 8/41* | (2006.01) | |
| *A61K 8/97* | (2017.01) | |
| *A61K 31/11* | (2006.01) | |
| *A61K 31/205* | (2006.01) | |
| *A61K 33/14* | (2006.01) | |
| *A61K 36/898* | (2006.01) | |
| *A61Q 5/00* | (2006.01) | |
| *A61Q 5/02* | (2006.01) | |
| *A61Q 19/00* | (2006.01) | |
| *A61K 8/46* | (2006.01) | |
| *A61Q 19/10* | (2006.01) | |

(52) U.S. Cl.
CPC ............... *A61K 33/02* (2013.01); *A61K 8/20* (2013.01); *A61K 8/416* (2013.01); *A61K 8/463* (2013.01); *A61K 8/97* (2013.01); *A61K 31/11* (2013.01); *A61K 31/205* (2013.01); *A61K 33/14* (2013.01); *A61K 36/898* (2013.01); *A61Q 5/00* (2013.01); *A61Q 5/006* (2013.01); *A61Q 5/02* (2013.01); *A61Q 19/00* (2013.01); *A61Q 19/007* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,800,087 A | 1/1989 | Mehta | |
| 4,822,604 A * | 4/1989 | Knoll | ...................... A61K 8/23 424/DIG. 4 |
| 5,104,645 A | 4/1992 | Cardin et al. | |
| 5,607,980 A * | 3/1997 | McAtee | ................. A61K 8/416 424/78.02 |
| 5,680,962 A * | 10/1997 | McEleney | ............ A61K 8/4973 222/129 |
| 5,997,889 A * | 12/1999 | Durr | ...................... A61K 8/671 424/401 |
| 6,585,983 B1 | 7/2003 | Gers-Barlag et al. | |
| 2001/0018059 A1 | 8/2001 | Gehlsen | |
| 2002/0111280 A1 | 8/2002 | Trage et al. | |
| 2002/0168423 A1 | 11/2002 | Wurzburger | |
| 2002/0173436 A1 | 11/2002 | Sonnenberg et al. | |

FOREIGN PATENT DOCUMENTS

| | | |
|---|---|---|
| EP | 1250915 A1 | 10/2002 |
| WO | 99/32084 A1 | 7/1999 |
| WO | 2000/000186 | 1/2000 |
| WO | 2002/055060 | 7/2002 |

OTHER PUBLICATIONS www.foodnetwork.com/food/recipes/recipe/0,,FOOD_9936_31228,00. html (2005).
Sunbum 2012, http://emedicine.medscape.com/article/773203-overview.
2010, http://dermnetnz.org/systemic/xeroderma-pigmentosum.html.

* cited by examiner

*Primary Examiner* — Terry A McKelvey
*Assistant Examiner* — Catheryne Chen
(74) *Attorney, Agent, or Firm* — Oliff PLC

(57) ABSTRACT

A product with an enhanced medicinal and cosmetic composition with a specific utility of "Psoriasis, Eczema and like skin disorders application" is characterized by the fact that it comprises active agents and ingredients as vanilla extract, ammonium chloride, potassium chloride and quaternary ammonium compound having formulated at a specific pH value with other specially selected adjuvants and fillers.

4 Claims, No Drawings

KERATOLYTIC COMPOSITION WITH ANTI-ALLERGIC ANTI-INFLAMMATORY PROPERTIES

FIELD OF THE INVENTION

The present invention relates to a pharmaceutical composition as well as pharmaceutical and/or cosmetic preparation that is effective for the treatment of psoriasis and like skin disorders.

BACKGROUND OF THE INVENTION

Epidemiological surveys have indicated an increase in allergic diseases. The increase in these allergic diseases has become a big social and economical problem and people and governments are losing time and money, besides having psychological affects.

It is believed that changes of environmental surroundings are the main cause for these diseases. Environmental changes such as migration to new places and climates, westernization of food, pollution, food additives, excessive use of cosmetics and medicines, excessive stress are the causes of an increase in such allergic symptoms.

Allergens are substances from foods, plants, environment or animals that inflame the skin because the immune system over-reacts to these substance. Inflammation occurs even when the person is exposed to very small amounts of the substance for a limited period of time. Some examples of allergens are pollen and pet's dander (tiny particles from the animal's skin or hair).

Allergic reactions are classified into from type I to type IV depending on the causative immunoglobulins and cells participating therein. The types I to III allergies are immunological reactions in which human antibodies participate. They are called immediate-type allergies, since allergic reactions appear immediately upon contact.

The type IV allergy is a cell-mediated immunological reaction in which instead of an antibody, sensitized lymphocytes participate. It is also called delayed-type allergy. Allergic reaction of type IV is a reaction of a delayed type in which T cells (small white blood cells that orchestrate and/or directly participate in the immune defenses, also known as T lymphocytes) receiving an antigen information via antigen-presenting cells and release various cytokines whereby an inflammation reaction of a delayed type takes place.

Allergic contact dermatitis is a typical disease, which occurs due to an allergic reaction of type IV. Steroid compositions are used for the therapy of allergic diseases of type IV and such steroid compositions suppress the production of cytokine in T cells and show a dramatic effect for the therapy of eczema. On the other hand however, there is a possibility that they cause severe adverse actions such as thinning/sensitizing of skin, sleeplessness, photosensitivity, decrease in adrenocortical function etc by long period administration.

An example of an allergic and immunology mediated skin disease is psoriasis. Recent researches indicate that psoriasis is likely a disorder of the immune system. This system includes a type of white blood cell, called a T cell, that normally helps protect the body against infection and disease. Scientists now believe that, in psoriasis, an abnormal immune system causes activity by T cells in the skin. These T cells trigger the inflammation and excessive skin cell reproduction seen in people with psoriasis. Many of the pathological and histological findings of this disease are equivalent to those of dermatitis (eczema). Psoriasis is frequently worsened and becomes chronic by external stimulus. In each case, it is the fundamental therapy to control the skin symptoms to thereby prevent worsening.

Common treatments for Psoriasis are corticosteroids, calcipotriene, anthralin, topical retinoid, coal tar, salicylic acid etc. All of these treatments have side effects and become ineffective when used in for long period of time.

Pharmaceutidal compositions for allergic and immunology skin diseases have already been developed and being used for the therapy but, they have adverse reactions hence, there has been a strong demand for compositions derived from natural products where a long-term administration is possible, safety is high and no adverse reaction takes place.

SUMMARY OF THE INVENTION

This invention provides a therapeutic and preventive composition for allergic and immunology skin diseases which has no adverse action, shows a high safety even by a long-term administration and is able to be utilized for pharmaceutical and/or cosmetic preparation and cosmetic composition which are used daily.

The present invention relates to a pharmaceutical composition as well as pharmaceutical and/or cosmetic preparation containing vanilla extract/oil or vanillin selected from natural or synthetic vanilla and derivatives thereof as an effective ingredient and, more particularly, it relates topical preparation having an action of keratolytic and/or suppressing the iminediate-type and delayed-type allergy and/or reducing inflamation, to a pharmaceutical composition with an object of improving the allergy and to a cosmetic composition containing the same.

This invention provides a therapy for prevention, reduction and relief of scaling of allergic and/or autoimmune skin diseases, such as psoriasis, pityriasis rosea, lichen planus, pityriasis rubra pilaris, dermatitis (eczema), acne, dandruff etc, which has no adverse action, shows a high safety even by administration for a long period and is able to be utilized as pharmaceutical and/or cosmetics, etc. which are used daily. To be specific, topical application provides keratolytic effect along with anti-allergic and anti-inflammatory effect and it is characterized in containing vanilla extract/oil or vanillin selected from natural or synthetic vanilla and derivatives thereof as an effective and/or active ingredient an anti-allergic composition for topical administration or an anti-inflammatory composition for topical administration which is characterized in containing vanilla extract/oil or vanillin selected from natural or synthetic vanilla and derivatives thereof as an effective and/or active ingredient to pharmaceutical and/or cosmetic preparation for it is useful in preventing, reducing or relieving allergic symptoms and/or inflammatory symptoms.

DETAILED DESCRIPTION OF THE PREFERRED EMBODIMENTS OF THE INVENTION

Natural vanilla has used for generations as flavoring in foods, drinks and medicines. Vanilla beans were an antidote for certain venomous bites. It was used for respiratory pain and congestion, deep coughs, stomach ailments etc. Presently vanilla finds its way mostly into food, cosmetic and medicines as flavoring agent and into perfumes and some medicines for its aromatic properties as mood enhancer/stimulant.

In the beginning of 1900s it was observed that workers who handled the pods of Vanilla Planifolia have developed dermatitis of the hands and face. Similar finding have been report by many others like Hutchinson (1892), Maiden (1912), White (1934), Downing (1939). This dermatitis was named as 'Vanillasim'. May be because of these finding it was never been used to cure any skin diseases. But most of the above findings are based on actual handling of vanilla pods, vines, plants.

In the present invention it has been found that when vanilla extract is used in the cleansing liquid where quantity is very minimal (say <2%) it exhibits an anti-allergic and anti-inflammatory effect on the skin in patients who suffer with psoriasis.

Most of the cleansing agents contain sodium chloride and/or ammonium chloride and/or potassium chloride. In the present invention it was found that when ammonium chloride is used along with other gentle surfactants like sodium laureth sulfate and ammonium laureth sulfate it was showing keratolytic properties by removing scales in psoriasis effected patients. The same test has been repeated by using sodium chloride in the place of ammonium chloride and found that it was not having keratolytic properties.

Ammonium chloride is being used presently in the cleansing liquids etc, but it has not been used as an ingredient specifically to provide a therapy for prevention, reduction and relief of scaling of allergic and/or autoimmune skin diseases. In addition to ammonium chloride other quartemary ammonium compounds, such as benzalkonium chloride, benzethonium chloride, cetalkonium chloride, cetrimide, cetrimonium bromide, cetylpyridinium chloride, glycidyl trimethyl, stearalkonium chloride, and the like can be used to like effect.

Though the actual mechanism is not understood, it was tested on 5 different patients with different climatic conditions and observed that cleansing composition containing ammonium chloride and/or ammonium surfactants and/or quarternary ammonium compounds exhibited keratolytic properties. Composition started showing anti-allergic and anti-inflammatory properties when natural vanilla extract was used in the composition.

It was also observed that composition exhibited better results when moisturizing natural extracts and/or oils like chamomile, sunflower, coconut etc are used in the composition preparation.

It was observed that vanilla, ammonium chloride and/or ammonium surfactants and/or quarternary ammonium compounds and other natural extracts like chamomile, sunflower, coconut etc exhibit keratolytic effect along with anti-allergic and anti-inflammatory effects and moisturizing the skin.

In order to illustrate the invention in detail, representative Examples will be given as hereunder although the invention is not limited thereto.

Example 1

For scalp cleansing composition:

| | |
|---|---|
| Ammonium Laureth Sulfate | 28-30% |
| Sodium Laureth Sulfate | 1-2% |
| Coamidopropylbetain | 2-3% |
| Ammonium Chloride | 0.50-1% |
| Tetrasodium EDTA | 0.25-1% |
| DMD Hydantoin | 0.10-0.40% |
| Citric Acid | 0.10-0.40% |
| Dye | 0.20-0.40% |
| *Vanilla* Extract | 0.10-0.30% |
| Chamomile Extract | 0.10-0.30% |

-continued

| | |
|---|---|
| Sunflower Extract | 0.10-0.30% |
| Deionised water | To make quantity to 100% |

Example 2

For Scalp Cream:

| | |
|---|---|
| Ammonium Chloride | 0.50-2% |
| Potassium Chloride | 0.50-2% |
| Citric Acid | 0.10-2% |
| *Vanilla* Extract | 0.10-0.50% |
| Chamomile Extract | 0.10-0.50% |
| Coconut Oil | 10-20% |
| Starch | 20-30% |
| White Soft Paraffin | 30-40% |
| Phenoxyethanol | 1-3% |
| Deionised water | To make quantity to 100% |

Example 3

For Body Lotion:

| | |
|---|---|
| Ammonium Chloride | 0.50-2% |
| Potassium Chloride | 0.50-2% |
| Citric Acid | 0.10-2% |
| *Vanilla* Extract | 0.10-0.50% |
| Chamomile Extract | 0.10-0.50% |
| Phenol | 0.10-0.50% |
| Talcum | 15-20% |
| Zinc Oxide | 5-10% |
| Glycerin | 7.5-15% |
| Alcohol | 20-30% |
| Deionised water | To make quantity to 100% |

Inventor himself is a psoriasis patient for the last 8 years. He tried all topical applications like salicylic acid, coal tar, steroid based etc and experienced all sorts of side effects associated with these presently available treatments.

This invention is lead by desire for developing a new and innovative treatment, which can be used in the longer periods of time without side effect associated with other products. The Topical Composition given in the example being used for more than 6 months and also tested on other psoriasis patients with encouraging results.

These compositions are convenient to use, cost effective compared to other preparations and most of all these can be used for longer periods of time without side effects.

The responsive time to the treatment may be different for each individual patient and depends upon the severity of the lesions. Typically some improvement is visible after 3-4 days after initiation of treatment.

Though the exact mechanism of action of quaternary ammonium compounds, such as ammonium chloride, and vanilla is not fully understood, actual testing on psoriasis patients have shown encouraging results without side effects associated with steroids and other presently available psoriasis topical applications.

It is also understood that each of above active ingredients described above, or two or more together may also find a useful application in other types of methods differing from the type described above.

While certain novel features of this invention have been shown and described and mentioned in the claims, it is not intended to be limited to the details above, since it will be understood that various omissions, modifications, substitutions and changes in the forms and details of the device illustrated and in its operation can be made by those skilled in the art without departing in any way from the spirit of the present invention.

What is claimed is:

1. A method of treating a skin disorder, the method comprising:
   administering to an area of skin exhibiting the skin disorder a composition comprising:
   active components that treat the skin disorder, the active components that treat the skin disorder consist of:
   at least one of vanilla extract, vanilla oil and vanillin in an amount of from about 0.1% to less than 2% by weight of the composition;
   quaternary ammonium in an amount from about 0.001% to about 40% by weight of the composition; and
   a cation chloride salt in an amount from about 0.001% to about 10% by weight of the composition, the cation chloride salt being selected from the group consisting of ammonium chloride and potassium chloride,
   wherein
   the skin disorder is selected from the group consisting of psoriasis, eczema, dermatitis, acne, and dandruff, and
   the pH of the composition is greater than about 3.0 and less than about 7.0.

2. The method of claim 1, comprising topically administering the composition on a daily basis for at least 4 days, to an area of skin exhibiting the disorder.

3. The method of claim 1, wherein the composition is topically administered in the form of a lotion, cream, ointment, emulsion solution, patch, pad, cleanser, conditioner, gel, soap, sprays, foam, or tape.

4. The method of claim 1, wherein the composition is a pharmaceutical or cosmetic preparation.

* * * * *